United States Patent [19]
Cullimore et al.

[11] Patent Number: 5,589,353
[45] Date of Patent: Dec. 31, 1996

[54] METHOD AND APPARATUS FOR THE SELECTIVE DETERMINATION OF FERMENTATIVE CULTURED ACTIVITIES

[76] Inventors: D. Roy Cullimore, 3303 Grant Road, Regina, Saskatchewan, Canada, S4S 5H4; George W. Alford, 1954 Old Daytona Rd., Daytona Beach, Fla. 32014

[21] Appl. No.: 450,420

[22] Filed: May 25, 1995

[51] Int. Cl.$^6$ .............................. C12Q 1/04; C12M 3/00
[52] U.S. Cl. ................ 435/34; 435/288.2; 435/288.5; 435/288.7; 435/304.2; 435/808; 422/101; 422/102
[58] Field of Search ................................ 435/34, 288.2, 435/288.5, 288.7, 304.2, 808; 422/101, 102

[56] References Cited

U.S. PATENT DOCUMENTS 4,906,566  3/1990  Cullimore et al. ................ 435/34
5,187,072  2/1993  Cullimore et al. ................ 435/34

*Primary Examiner*—David A. Redding
*Attorney, Agent, or Firm*—James B. Middleton

[57] ABSTRACT

A test device provides an enclosed culture device for safe determination of the presence of a targeted microorganism. A test chamber is concentrically received within a culture chamber, and caps allow selective opening of one chamber without opening the other. A window in the test chamber allows selective flow of liquid between chambers, the window being so placed as to require particular manipulation of the chambers. The test chamber contains a culture medium and, through appropriate manipulation, a sample in the culture chamber is caused to wet the culture medium. The device is then incubated, and the sample in the culture chamber maintains high humidity in the test chamber because of the window. A pre-treatment vial is also provided so the sample can be treated before being placed into the culture chamber, to eliminate interfering organisms or the like.

12 Claims, 3 Drawing Sheets

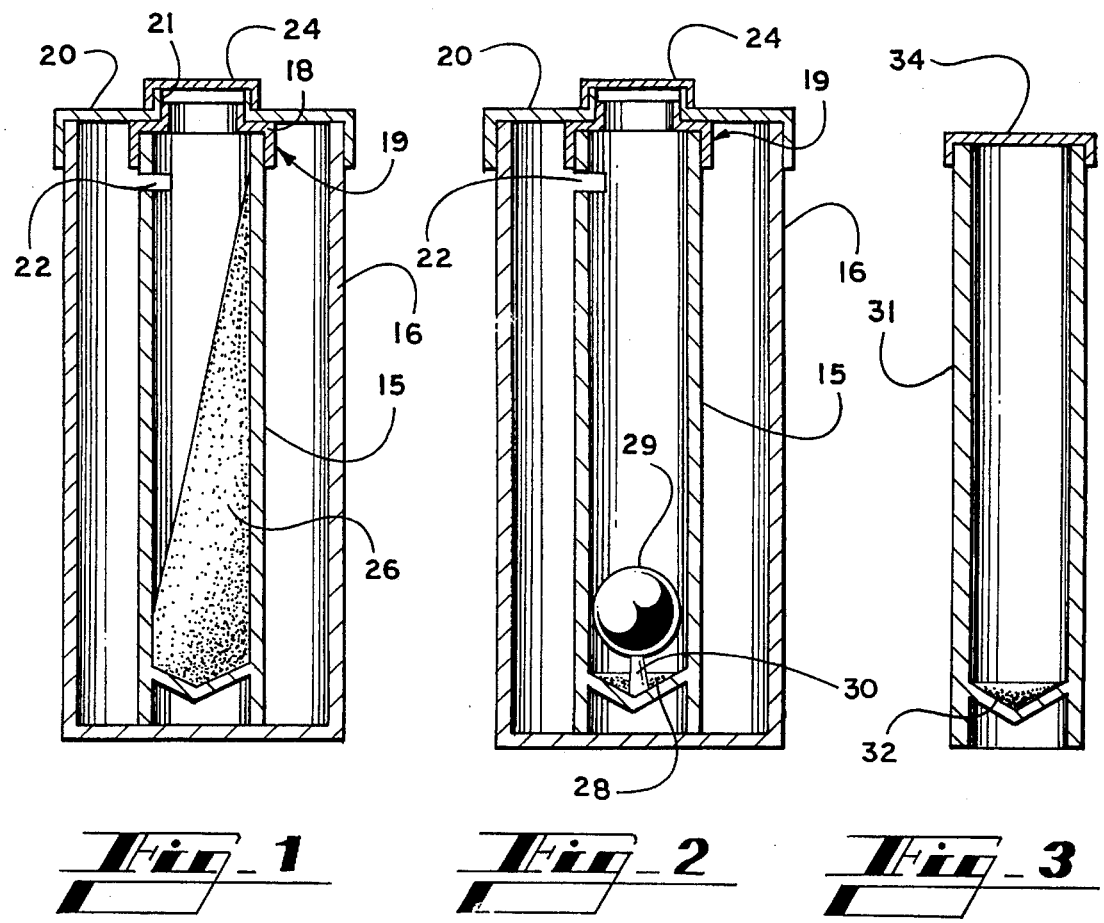
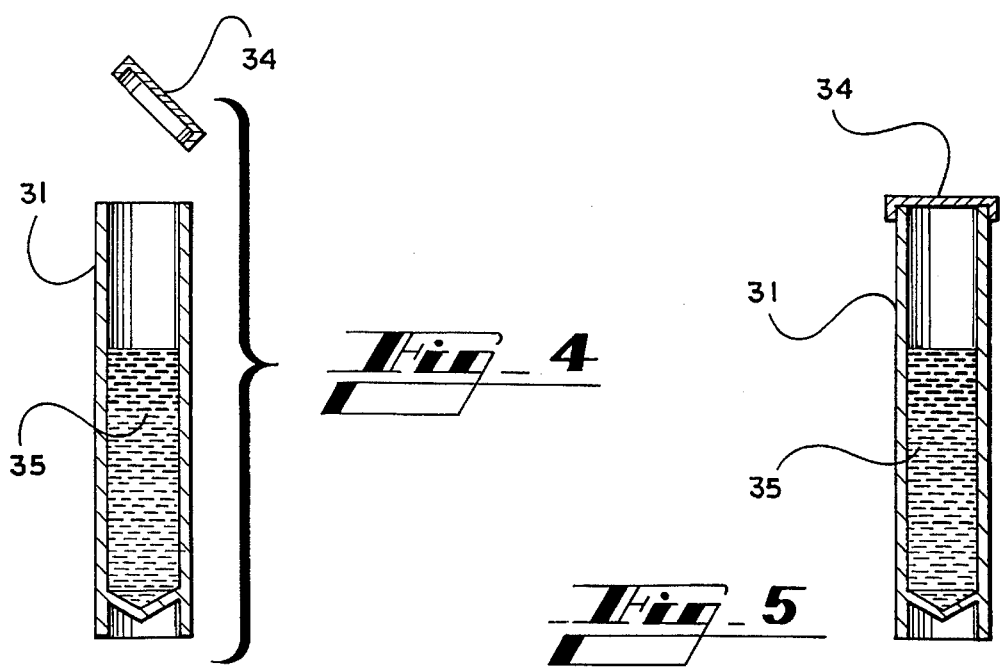
Fig_1   Fig_2   Fig_3
Fig_4   Fig_5

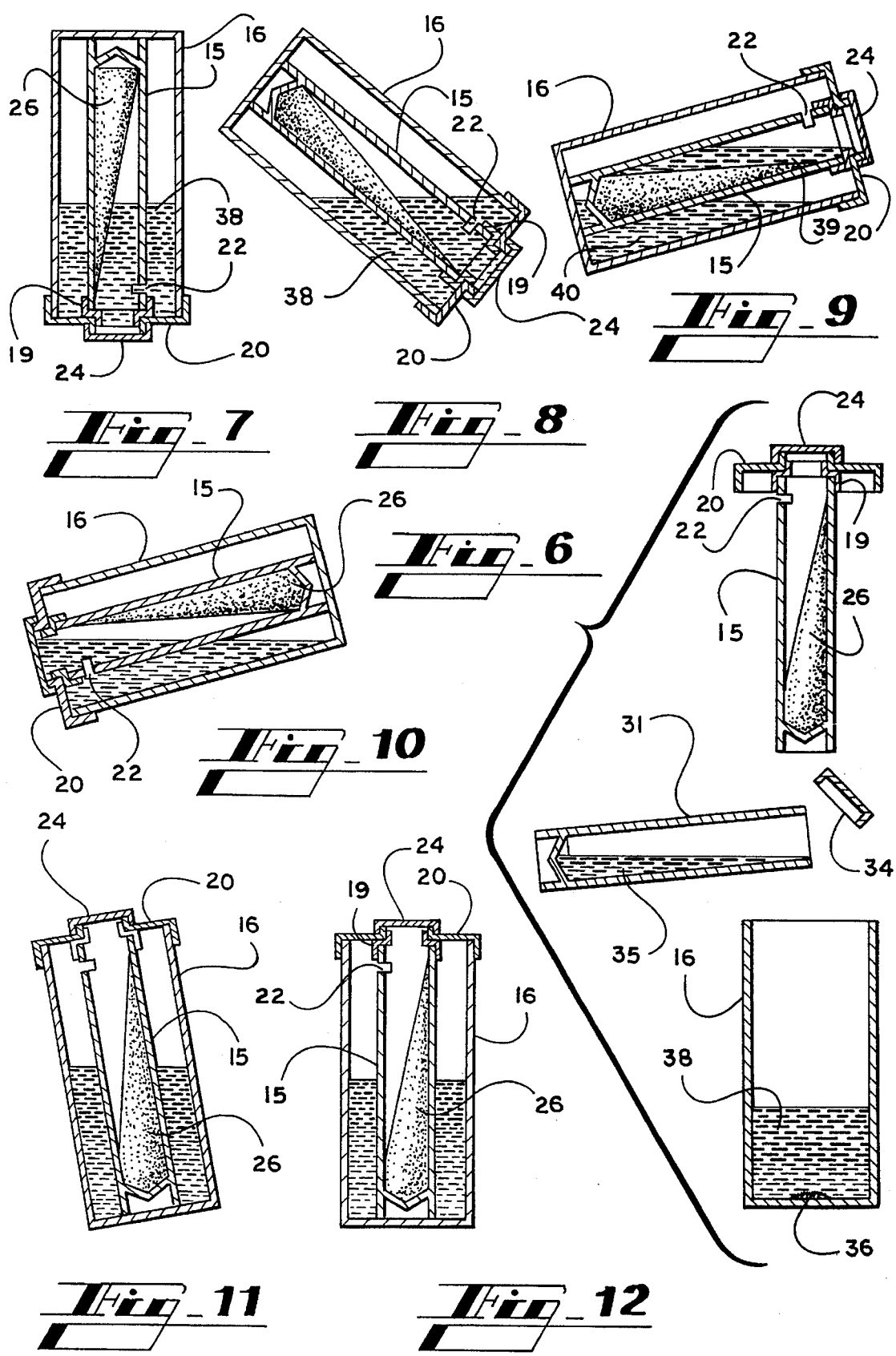

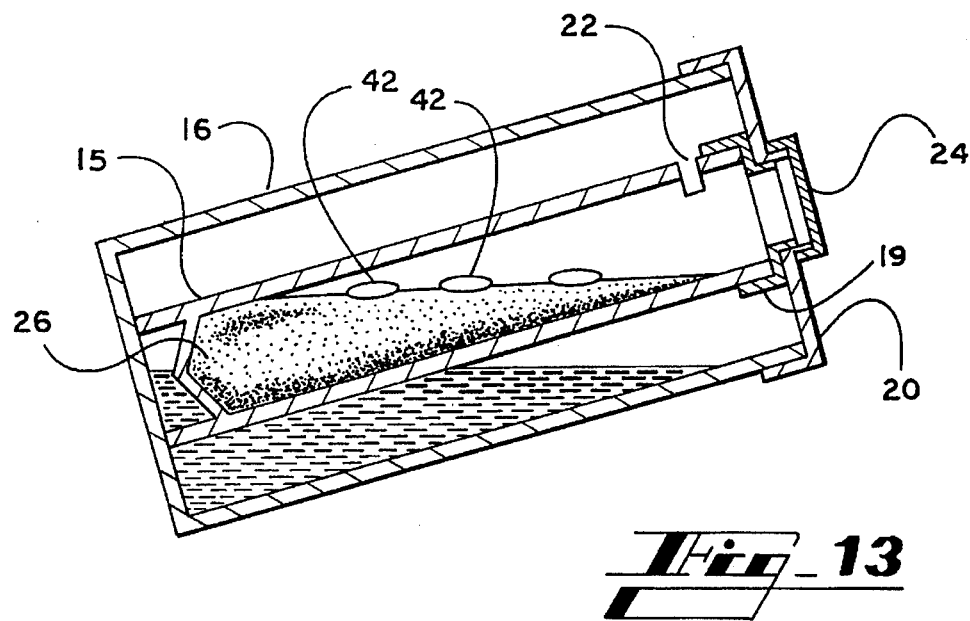
Fig_13
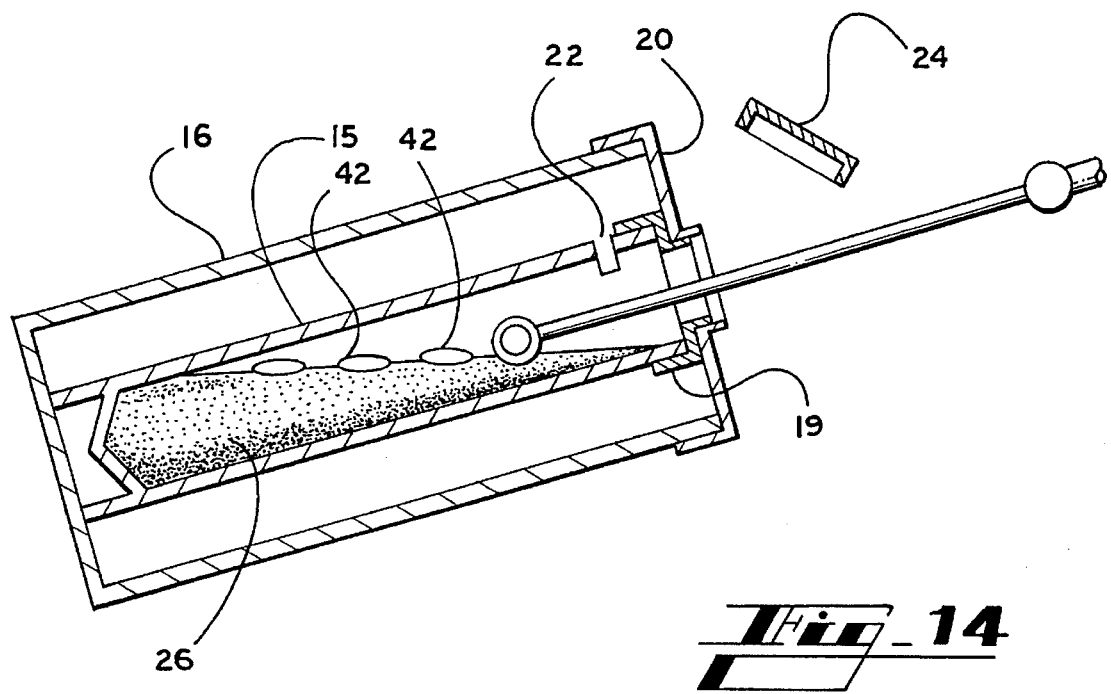
Fig_14

METHOD AND APPARATUS FOR THE SELECTIVE DETERMINATION OF FERMENTATIVE CULTURED ACTIVITIES

INFORMATION DISCLOSURE STATEMENT

1. Field of the Invention

This invention relates generally to a method and apparatus for performing microbiological analysis, and is more particularly concerned with an appropriately sequenced cultural method and apparatus for the screening of a sample to determine the presence of an organism of choice.

2. Discussion of the Prior Art

Recent advances in microbiology have engendered many techniques useful to the engineer, microbiologist and various health specialists. A large number of tests is conducted daily, both in the field and in the laboratory. With the increasing awareness of the greater diversity in sources of microbially driven compromises of systems and infections, there is an accelerating demand for screening of substances, notably water and pathologic material, to ensure the accurate determination of cause for a given economically significant compromise or clinically important infection. However, due to the time required for these tests, and the cost of such tests, complete testing is not economically feasible so that the tests may be run only on substances already under suspicion because of various inferential evidence.

Those skilled in the art will realize that an incipient problem may not manifest itself in the natural state for one or more of a variety of reasons, but the contamination may become obvious after some inferences in the natural system. By way of example, bacteria may be present in small quantities, but may not be readily detectable through some understood biochemical or cultural function due to direct or indirect interferences from other organisms present, through the inadequate ability of the conventional cultural devices and/or biochemical screening techniques to display some form or other of affirmative occurrence, or through cultural conditions unsuitable to the yielding of a response.

The prior art includes cultural systems utilizing various solid, semi-solid or liquid media as, or within, supportive media which yield a response, the response being relatable to the presence and/or activity of the organisms active in association with the presence of these various forms of media. Most commonly, an agar-based culture medium is employed where the organism of choice will, under favorable circumstances, form a visible presence as a discrete and definable colonial form which can be enumerated. Another common, but less quantifiable, methodology widely practiced is the use of liquid cultural media within which the activity of the organisms is generally manifested in the qualitative form. The prior art in general does not present systems or devices which, of themselves, are able to incorporate conditions considered to be the most suitable for the detectable activities of the organism of choice, while providing convenience and safety to the operator of the device, either in the field or in the laboratory environment. The prior art further calls for the preparation of the sample in a manner which generates a limitation of the technique to those skilled in the art.

Information disclosing prior art can be found in the following articles:

ZAPFFE, F. C (1903) Bacteriology, A Manual for Students and Practitioners. Published by Lea Brothers & Co., Philadelphia. 350 pp.

BARON, E. J. et al. (1994) Medical Microbiology, A Short Course. Published by Wiley-Liss, New York. ISBN 0-471-56728-0. 1057 pp.

CULLIMORE, D. R. (1993) Practical Manual of Groundwater Microbiology. Published by Lewis Publishers, Boca Raton. ISBN 0-87371-295-1. 412 pp.

SUMMARY OF THE INVENTION

The present invention provides a method whereby a sample may be pre-treated, applied to selected conditions for culture, and sequentially moved in such a manner as to encourage the activities that will determine, in a qualitative and/or quantitative manner, the presence of the organism of choice without undue interference from other organisms that may be present in the original sample.

The present device provides a dual, concentrically arranged pair of chambers interconnected by a selectively placed window through which gases and liquids can freely flow, when the device is appropriately inverted. While the inner chamber is designed to allow the determination of the cultured diagnostic activities of the organism of choice, the outer chamber is designed to allow the pre-treatment of the sample prior to admission of the sample to the inner chamber for the determination of the selected activities. After admission of the pre-treated sample to the inner chamber and the associated inoculation of the culture medium with organisms form the sample, the sample can be returned via the elevated window to the outer chamber for storage. This use of the outer chamber as a storage site for the sample during the culture of the organisms within the device serves two primary functions which are to maintain a high relative humidity within the device and to retard evaporation of water from the media within the inner chamber, and to provide security for the sample during the test period. Should the sample contain organisms that present a potential risk of any type to the user of the device, such organisms will be confined within the device until suitable disposal can be arranged. To determine the nature of the potentially diagnostic events which may be occurring within the inner chamber, the device can be tilted to allow a view of the inner chamber unimpeded by the presence of the water sample retained within the outer chamber.

BRIEF DESCRIPTION OF THE DRAWINGS

These and other features and advantages of the present invention will become apparent from consideration of the following specification when taken in conjunction with the accompanying drawings in which:

FIG. 1 is a diametrical cross-sectional view of a culture chamber having a test device therein made in accordance with the present invention, and including the final volume of culture medium presented as an agar slant;

FIG. 2 is a modified form of the device shown in FIG. 1, showing the culture medium as a dried deposit within the test device;

FIG. 3 is a diametrical cross-sectional view of a vial incorporating a selective chemical pellet which may be used to pre-treat the sample before placement within the culture chamber shown in FIG. 1;

FIG. 4 is similar to FIG. 3, but showing a sample in the test vial shown in FIG. 3;

FIG. 5 is similar to FIG. 4 and illustrates the retention of the sample within the vial for a sufficient time, and under suitable conditions, to allow the pre-treatment to be effective in accordance with the established protocol;

FIG. 6 is an exploded, diametrical cross-sectional view of the culture chamber showing the sample, whether pre-treated or not, being dispensed into the outer part of the culture chamber;

FIG. 7 shows the culture chamber of FIG. 6 re-assembled after the sample has been added, the whole chamber being inverted to allow the sample to pass through the window into the test device;

FIG. 8 illustrates a method by which the culture chamber can be manipulated to allow at least a known and definable part of the sample to flood over the culture agar slant and allow an opportunity for any organisms within the sample an opportunity to attach to the culture medium;

FIG. 9 illustrates the sample in part flooding the culture agar medium to allow attachment by the organisms to occur while the remainder of the sample is entrapped within the outer chamber;

FIG. 10 is the lateral reverse of FIG. 9 showing the sample moved away from the culture agar medium and towards the window to become confluent with the sample retained within the outer chamber;

FIG. 11 is a diametrical cross-sectional view similar to FIG. 1 showing the outer chamber retaining the sample while the culture chamber is incubated in a manner conducive to the culture of the organisms of choice, the device being mostly righted from the position of FIG. 10;

FIG. 12 is similar to FIG. 11, but showing the device fully righted;

FIG. 13 is a cross-sectional view showing the culture chamber angled to allow an observer a clear view through the walls of the device without interference from the sample still retained within the outer chamber of the device; and, FIG. 14 illustrates the removal of the capping device from the culture chamber so that discrete samples of the cultural activities can be withdrawn for subsequent evaluation and such confirmatory procedures as may be considered appropriate.

DETAILED DESCRIPTION OF THE EMBODIMENTS

Referring now more particularly to the drawings, and to those embodiments of the invention here presented by way of illustration, the embodiment of the invention shown in FIG. 1 includes a test device 15 within a culture chamber 16. The physical arrangement is such that the test device 15 is prevented from taking up a lateral position due to the hollow tube-like extension 18 of the cap 19 which is affixed to the test device 15. The cap 20 on the outer chamber 16 has a similar but larger hollow tube-like extension 21 which causes the test device 15 to become rigidly emplaced within the culture chamber 16. The test device 15 may be cylindrical in form as shown, and may have an opening or window 22 close to, partially within, or abutting the lower edge of the cap 19. The purpose of the window 22 is to allow free movement of atmospheric gases or liquids between the chamber within the test device 15 and the outer, concentric culture chamber 16 as the conditions permit.

To seal the culture chamber 16 and the test device 15 from the outside environment, a cap 24 is fitted tightly to the outer edge of the upper tube-like extension 21 on the cap 20. The suitable culture medium applicable to the successful culture of the organism of choice is presented as an agar slant 26. It should be understood by those skilled in the art that the agar medium, where employed, does not necessarily have to be in the form of a slant, and that this illustration is simply an example of one possible technique.

In FIG. 2, an alternative test device is shown. The physical structure of the culture chamber and the test device are the same, and the same reference numerals are applied. The device in FIG. 2, however, utilizes a selective culture medium in the form of a dried chemical pellet 28 set below a floating intercedent device 29. The intercedent device 29 is held up from contact with the chemical pellet 28 by a raised pillar 30. When a liquid sample is admitted to the device of FIG. 2 so the intercedent device will float and become elevated, gradients will be generated, associated with diffusion of the administered chemicals and the gases within the device throughout the medium, thus generating alternate potential environmental sites for cultural activities. The use of an intercedent device is discussed further in U.S. Pat. No. 4,906,566, and that disclosure is incorporated herein by reference.

In some circumstances the sample may need to be pre-treated before being admitted to the culture chamber 16. FIG. 3 illustrates a pre-treatment vial 31. The base of the vial 31 includes chemicals here shown as in the form of a pellet 32 at the bottom of the vial 31. The chemical of the pellet 32 will react with the sample in such a manner as to selectively reduce the risk of contaminant organisms' interfering with the efficacy of the test. The vial 31 is closed by cap 34 which can form an effective hydraulic seal during the pre-treatment phase of the test procedure when this is desirable.

FIG. 4 shows the vial 31 after the sample has been added for pre-treatment, the cap 34 being removed to allow the water sample 35 to enter and partially fill the vial 31 to a degree convenient for the particular act desired. The chemicals, where these are used in the pre-treatment, dissolve from the pellet 32 as illustrated in FIG. 3. This step is followed by a holding period as illustrated in FIG. 5. During the holding period, the chemicals from the pellet 32 diffuse up and through the sample 35 to form a concentration gradient. It will be readily recognized that the act of shaking the vial 31 will cause a more rapid and even mixing of the diffusing chemicals from the pellet 32.

Once the terms established in the specific protocol for pre-treatment have been met, then the act of admitting the treated sample to the test device is undertaken. This is illustrated in FIG. 6. To undertake the act of admission of the sample to the test device, the cap 20 which seals the outer chamber 16 is removed. Because of the tightness of fit of the cap 20, the test device 15 is elevated along with the cap 20, allowing direct admission of the pre-treated sample to the outer chamber 16. On such occasions as may be deemed necessary by those skilled in the art, a pellet of chemicals 36 may also be present. The additional chemical 36 can be used to neutralize possible undesirable effects from products of the pre-treatment, or as a further chemical pre-treatment when desirable.

The cap 34 is removed from the pre-treatment vial 31 and the contents 35 poured into the outer culture chamber 16. The chemicals 36, when employed, will either casually diffuse or be actively admixed with the sample to form a sample now designated at 38. This resulting sample may, after the requisite period of time, be administered to the test device.

To charge the test device with the prepared sample, a number of steps are normally required, and these are illustrated in FIGS. 7 through 12 inclusive. It will be understood by those skilled in the art that the example presented utilizes a selective agar culture medium. Examples of other formats of selective culture will be given below after this illustration of the agar device format. Once it is assured that the caps 19 and 20 (along with the central cap 24 which closes the central core of the other caps) are securely sealed, the culture chamber 16 including the pre-treated sample 38 is inverted as shown in FIG. 7. This causes the sample 38 to flood to the other end of the outer chamber, where the window 22 allows some of the sample to flow into the test device 15. The amount of the sample to enter the test device 15 can be designed to be a specific quantity of the sample material by the appropriate configurational dimensions of the device.

A part of the sample material 38 is now within the test device 15 and it is necessary to perform such maneuvers as will allow the organisms of choice, when present in the sample 38, an opportunity to attach to and be cultured on the selective agar culture medium presented as an agar slant 26.

FIG. 8 illustrates the device wherein the sample 38 is differentiated into two components, with one part inside the test device 15 while the remainder is cloistered within the outer chamber 16 of the culture device. As the culture device is lowered to a horizontal position with the window 22 on the uppermost side of the test device, the sample will become physically separated as subsample 39 within the test device 15, while the remainder of the sample 40 is retained within the concentric outer chamber of the culture chamber 16. Generally it may be expected that the act of rotating the culture device in this manner can be expected to increase the volume in the test device 15 in a reasonably predictable form so that the volume of water held within the test device may be expected to increase beyond the initial entrapped volume. By careful design of the form of the window, as to its shape, contour, and relationship to the vertical walls of the test device, the entrapped volume can be controlled and wholly predictable. In the example illustrated, the window 22 is rectangular and conforms to the circular contour of the vertical wall of the test device. This rectangular window 22 has a ratio of 5:3 in terms of lineal width:height, the upper edge of the window is about one millimeter below the lower edge of the cap 19, and the height of the window is ten millimeters. Those skilled in the art will understand that other specific dimensions can be selected based on this concept. Variations include, but are not limited to, the use of a flattened planar surface on the vertical wall of the test device below the window to increase the available volume of the outer chamber and improve the ease of direct observation of the contents of the test device; and the shifting of the window from a vertical to an angled perspective on the test device. Furthermore a second window may be employed to act as a venting device for more precise control of the volume of sample being admitted to the test device.

Once the test device containing the sample is further rotated beyond the position shown in FIG. 8, still with the window 22 uppermost, to allow the capped end of the culture chamber to move to a higher plane than the base, the sample becomes physically separated into two parts as illustrated in FIG. 9. The part 39 of the sample now floods over the selective agar culture medium 26 while the remaining part 40 falls and occupies the lowest points of the outer chamber 16. This allows two events to happen. Firstly, that part of the sample which is within the test device as 39 falls into intimate contact with the surface of the agar 26 which allows a time period wherein the organisms of choice can become attached by any means to the surface layers of the agar in manners that will prevent their removal when the sample is drained from the site. Such forms of attachment and subsequent colonial forms of growth are well known to those skilled in the art. Secondly, the window 22 is raised out of the sample and connects the atmosphere between the inner test device 15 and the outer culture chamber 16. By the appropriate admission of chemicals in pellet 36 (see FIG. 6) to the outer chamber, it becomes possible to generate reactions, once wet with the sample material, which can lead to a modification of the atmosphere within the culture chamber by such events as the release of carbon dioxide gas. Enhanced carbon dioxide levels are known to encourage the growth of some microorganisms. The sample 39 is left in contact with the agar surface 26 for a period of time, after which the sample is withdrawn by further manipulations of the culture chamber in the manner illustrated in FIGS. 10 through 12 inclusive.

To remove the surplus of sample 39 that has not adhered in any manner to the surfaces within the test device, the culture chamber is rotated on its horizontal axis with the window side facing downwards as in FIG. 10, with the capped end of the chamber tilted slightly downwards. The sample 39 within the test device 15 flows away from the agar surface 26 to collect around the window 22 and reconnect with the sample resident in the outer chamber. As the culture chamber is carefully returned to a vertical position as illustrated in FIG. 11, the sample collects in the base of the outer culture chamber 16, leaving the agar surface 26 free of surplus non-adherent sample material. Once the culture chamber is returned to the full upright position as shown in FIG. 12, the sample that has not adhered in any manner inside the test device collects within the outer culture chamber 16 leaving the elevated window 22 in the test device exposed to atmospheric flows between the outer culture chamber 16 and the inner test device 15. The culture chamber can now be incubated in a manner to support the recognizable activities of the organisms of choice on and within the agar surface 26. A very humid atmosphere is created for this incubation by the resident sample occupying the lower regions of the outer culture chamber. At the same time, the atmosphere within the culture chamber may be influenced by reactions and activities generated by the organisms within the chamber and by further chemical activities that may have been deliberately instituted through additions of specific chemicals to the culture chamber at some point before, during or after the incubation period.

The diagnostic activity where the organisms of choice are present and are active would commonly be in the form of either direct and distinct forms of colonial growths and/or recognizable interactions with the agar medium on and/or within the activity occurring. As illustrated in FIG. 13, the culture chamber may be conveniently observed for such events by tilting the chamber 16 at a slight angle from the horizontal with the window 22 in the test device uppermost, and the resident sample material resting in the outer chamber 16 below the test device 15 and out of the direct line of vision between the observer and the surface of the agar medium 22. Colonial growths 42 and other recognizable activities related to organisms adherent to the culture agar medium can now be viewed conveniently. If it is desirable to remove a part of the colonial growth 42 or sites of activity from the test device 15, a portal of entry is provided as shown in FIG. 14. To remove material from the test device 15, the central uppermost cap 24 is removed and a suitable implement such as a bacteriological loop can be inserted into the test device 15 through the opening. Specific material can therefore be removed for further scientific examination and/or testing by conventional methods known to those skilled in the art.

In normal circumstances, the culture apparatus will be shipped with the culture medium in either the dried or prepared agar form. Adjunct chemicals sited elsewhere within the culture chamber or the pre-treatment vial would normally be in a dried form. The contents of the vial 31, culture chamber 16 and test device 15 would normally be sterile unless a specific technique called for the deliberate addition of a culture as a part of the protocol recommended for the recognition of the size and/or activity level of the targeted organisms where present in the sample. Practice of this invention contemplates making the test results (automatic or manual) comparable to graphically presented standards along with tables, descriptors and protocols where required. Users would be encouraged to undertake comparable controls.

It will be recognized that the present invention may be utilized in a number of manners, each of which will utilize some of the unique features which form a part thereof. Below are given examples of alternative protocols that may be accomplished using the culture chamber with or without the additional pre-treatment vial.

In the first example of an alternative protocol, the test device is prepared in the format shown in FIG. 2. The sample may be subjected to an assay for the effectiveness of a specific biocide which is applied at a specific rate to a known volume, for example 30 ml, sample from a chemical pellet 32 present in the pre-treatment vial 31. On admission of the pre-treated sample to the culture chamber 16 in the manner illustrated in FIG. 6, a neutralizing chemical to the biocide incorporated into the chemical pellet 36 held within the outer culture chamber negates the activity of the biocide being evaluated. Once this activity is negated, the sample can be admitted to the test device using the methodology illustrated in FIGS. 8 and 9, but with the device designed in such a manner that allows 15 ml or other suitable volume of sample to be retained within the test device 15 during the incubation period. Incubation would be with the culture chamber in a similar mode to that shown in FIG. 12, but the sample would be divided in a pre-ordained manner between the outer chamber 16 and the test device 15 so as to allow such activities as are desirable to occur where the targeted organisms are present.

A second example relates to the need on occasions to undertake a serial dilution of the sample using a suitable diluent with each diluent in the series being subjected to a determination of the size and/or activity level of the targeted organisms within each diluent. Such methodologies are known to those skilled in the art, to determine quantitative information concerning the targeted organisms. In this example, the series of diluents of the sample would be prepared nominally as a tenfold series of 9 ml dilutions. To each of the sequences of culture chambers being utilized for this procedure, the following protocol would be used based upon modifications of the procedures already discussed above. To undertake this example, the uppermost sealant cap 24 will be removed and the 9 ml of the diluent selected for this specific test will be added. In the event that the test device contains a selective agar culture medium, the diluent will be allowed to remain in contact with the medium for a suitable period of time to allow organisms to adhere by any means to the surface layers of the agar. Once this has been accomplished, the remaining diluent sample will be removed from the test device using the technique illustrated in FIGS. 10 to 12. During the subsequent incubation period the diluent sample outside of the test device will aid in the maintenance of the humidity within the test device and cause modifications to the atmosphere within the culture chamber which would be potentially beneficial to the culture of the targeted organisms.

As can be seen from the foregoing description, the present invention involves a number of stages in the conducting of the testing procedure which generates advantages both from the perspective of user convenience and also from the perspective of selective culture of the targeted organism. For the user, the procedure using the devices described above can manipulate the sample through pre-treatment to inoculation and incubation of the culture chamber with convenience and a minimum level of risk which may be present in the sample or subsequently generated through the cultural activities of the organisms from within the sample during incubation and observation. The use of a double walled container which is capped reduces the risk of leakages, while the retention of the sample within the device reduces the disposal risk to the final event which should be performed by someone familiar with the art of safe disposal. Four advantages presented in this form of the culture chamber are: the ability to pre-treat the sample either in the vial 31 or in the outer chamber 16; the elevation of the humidity within the culture chamber due to the retention of the sample within the outer chamber will reduce the degree of desiccation which would otherwise present a risk of compromising the cultural qualities of the culture agar medium; by reaction between the water and the dried chemical pellet 36 when present in the outer chamber which could cause evolution of such gaseous substances as carbon dioxide which could then stimulate the growth of the targeted organism; and, the uppermost cap 24 provides a convenient means through which selected parts of the cultured activity can be recovered for further study, such as in the form of smears from colonies which have formed on the culture agar medium.

By way of an example of the use of the culture chamber in a manner appropriate to the descriptions of this invention, the application of the technique will be described for the determination of the presence or absence of the bacterial species *Legionella pneumonophila*, the recognized infectious agent that causes Legionnaires' disease, the disease beginning as a characteristic pneumonia, often followed by multiple system damage, such as renal failure and diarrhea. In this event, the pre-treatment will involve the vial 31 in which the chemical pellet 32 contains such chemicals as will ionically create sulfuric acid. This acidulation will lower the pH of the sample to between 1.5 and 2.0. The lowered pH will be extremely traumatic for the incumbent organisms in the sample. *Legionella pneumonophila* however is known to be acid-tolerant and therefore will be less affected than other organisms that may be present in the sample. After a specified period of time, such as fifteen minutes, the acidulated sample will be transferred to the outermost culture chamber of the device. Here, basic chemicals 36 will react with and neutralize the acids in the sample with a concomitant release of carbon dioxide. It is recognized by those skilled in the art that elevated carbon dioxide levels, such as of 5%, are beneficial to the culture of *Legionella pneumonophila*. The culture agar medium used in this example will be Buffered Carbon Yeast Extract (BCYE) agar. Incubation will be at 35° C. for ten days. The highly humidified atmosphere created by the presence of the residual sample within the outer chamber will enhance the culture of *Legionella pneumonophila*. Typical colonies formed will be ground-glass appearing, white to shades of blue, green, or purple, often fluorescing under ultra-violet (UV) light. Such typical colonies can be selectively removed using the technique illustrated in FIG. 14 and sent to a reference laboratory where they can be identified serologically. This device therefore supports a technique which can more conveniently and reliably determine the presence of *Legionella pneumonophila* in samples.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

We claim:

1. A test apparatus, for use in determination of the presence of a targeted microorganism within a given sample, said test apparatus comprising a test chamber having a wall and an open top, said wall defining a window therein, and a culture chamber, said culture chamber being of sufficient size to receive said test chamber therein, and having a wall and an open top, a first cap means receivable on said open top of said culture chamber for closing said open top of said culture chamber, and second cap means for closing said open top of said test chamber, said window being so placed as to allow communication between said test chamber and said culture chamber when said test chamber is within said culture chamber and said first and second cap means are in place.

2. A test apparatus as claimed in claim 1, and further including a third cap means, said third cap means being receivable over said open end of said test chamber, said third cap means defining a central opening, an upwardly extending flange surrounding said central opening, said first cap means defining a central opening therein concentric with said central opening of said third cap means and sized to receive said upwardly extending flange of said third cap means.

3. A test apparatus as claimed in claim 2, said first cap means including an upwardly extending flange surrounding said central opening, said second cap means being receivable over said upwardly extending flange.

4. A test apparatus as claimed in claim 1, and further including a culture medium within said test chamber.

5. A test apparatus as claimed in claim 4, wherein said culture medium comprises an agar slant.

6. A test apparatus as claimed in claim 4, wherein said culture medium comprises a pellet within said test chamber.

7. A test apparatus as claimed in claim 6, and further including a floatable intercedent device within said test chamber, said intercedent device being floatable in said given sample.

8. A method for testing a sample for the presence of a targeted microorganism, said method comprising the steps of placing said sample into a culture chamber, placing a test chamber within said culture chamber, said test chamber having a culture medium therein, and having a window in the wall thereof, capping said test chamber and said culture chamber, and inverting said test chamber and culture chamber so that at least some of said sample will pass through said window and into said test chamber, and manipulating said test chamber and culture chamber so that said sample flows onto said culture medium.

9. A method as claimed in claim 8, and further including the step of pre-treating said sample before the said step of placing said sample into a culture chamber.

10. A method as claimed in claim 8, and including the step of subsequently manipulating said test chamber and culture chamber so that said sample flows away from said culture medium and into said culture chamber.

11. A method as claimed in-claim 10, and further including the step of incubating said test chamber and culture chamber with said sample within said culture chamber so that vapor can pass through said window for humidifying said test chamber.

12. A method as claimed in claim 11, and including the step of opening said test chamber while retaining said culture chamber in a closed condition, for selective removal of cultures grown within said test chamber.

* * * * *